United States Patent
Menendez Martin et al.

(10) Patent No.: US 7,497,115 B2
(45) Date of Patent: Mar. 3, 2009

(54) QUALITY CONTROL PROCESS FOR A STRUCTURAL BONDED JOINT

(75) Inventors: José Manuel Menendez Martin, Madrid (ES); Julián Sánchez Fernández, Madrid (ES)

(73) Assignee: Airbus Espana, S.L., Madrid (ES)

( * ) Notice: Subject to any disclaimer, the term of this patent is extended or adjusted under 35 U.S.C. 154(b) by 62 days.

(21) Appl. No.: 11/516,028

(22) Filed: Sep. 5, 2006

(65) Prior Publication Data

US 2008/0011075 A1    Jan. 17, 2008

(30) Foreign Application Priority Data

Jun. 30, 2006    (ES)  ............................... 200670092

(51) Int. Cl.
     *G01N 19/04*    (2006.01)
     *G01N 3/08*    (2006.01)

(52) U.S. Cl. ...................... 73/150 A; 73/827

(58) Field of Classification Search .................. 73/827, 73/150 A
See application file for complete search history.

(56) References Cited

U.S. PATENT DOCUMENTS

| 4,291,081 | A * | 9/1981 | Olez ........................ 428/119 |
| 4,993,268 | A * | 2/1991 | Thompson .................. 73/827 |
| 6,686,057 | B2 * | 2/2004 | Wang ........................ 428/593 |
| 6,846,039 | B2 * | 1/2005 | Lewno ....................... 296/201 |
| 7,162,929 | B2 * | 1/2007 | Tandon ...................... 73/827 |
| 2007/0044569 | A1 * | 3/2007 | Hutter, III ................... 73/827 |

* cited by examiner

*Primary Examiner*—Harshad Patel
*Assistant Examiner*—Jonathan Dunlap
(74) *Attorney, Agent, or Firm*—Ladas & Parry

(57) ABSTRACT

The invention relates to a quality control process for an adhesive joint of two sub-components of a structure comprising the following steps: a) Providing the structure of composite material to be controlled; b) Providing at least one premanufactured testing device (1) representative of one of the sub-components of the structure; c) Bonding the at least one premanufactured testing device (1) to the other sub-component (7) of the structure in conditions similar to those of the real adhesive joint of the sub-components; d) Carrying out at least one mechanical test on the at least one premanufactured testing device (1) which allows assessing the quality of the adhesive joint.

14 Claims, 6 Drawing Sheets

QUALITY CONTROL PROCESS FOR A STRUCTURAL BONDED JOINT

FIELD OF THE INVENTION

The invention is included within the field of manufacture of structures incorporating joint consolidation processes of several sub-components (for example, co-curing of sub-components of structures of composite material formed by a discontinuous reinforcement of fibers or the like and a continuous matrix of thermoset resin or the like) and/or adhesive-joints of several sub-components (for example, bonding of sub-components of structures of composite or metallic materials), specifically in those technological areas requiring additional tests of standard test coupons representative of said joints certifying the quality thereof due to safety issues.

BACKGROUND OF THE INVENTION

The intensive introduction of advanced composite materials in primary structures has become a fundamental procedure for structural optimization (based on weight saving and the improvement of mechanical properties), one of the priority objectives in the design and manufacture of a new generation of aircrafts.

One of the main advantages of introducing composite materials is the cost saving in assembly operations due to the high degree of integration of structural elements generally consisting of a skin and reinforcing or stiffening elements integrated in a consolidation and/or bonding process.

These adhesive joints, having numerous advantages compared to traditional riveted joints (they save in assembly operations, they are lighter, more rigid and have lower stress concentrations, they are leak-tight, etc), have an important drawback: both the materials used in said joint and the environmental conditions and handling conditions must be perfectly controlled at all times and the manufacture and testing of test coupons representative of said joint is necessary to assure the quality thereof.

The cost of the manufacturing and testing process of these test coupons is high, it further being difficult to assure that the configuration of the test coupons and manufacturing conditions are identical to those of the represented part, therefore the results obtained are only an approximation to the real conditions of the represented joint.

Therefore, the industry demands new quality control processes for adhesive joints which do not have the drawbacks set forth and the present invention is directed towards satisfying this demand.

SUMMARY OF THE INVENTION

In view of the above, it is an object of the invention to provide a quality control process for adhesive joints using premanufactured devices representative of one of the sub-components of the adhesive joint, which would be bonded to the other sub-component in conditions similar to those of the represented adhesive joint.

This objective is achieved by means of a quality control process for an adhesive joint of two sub-components of a structure, comprising the following steps:

a) Providing the structure of material to be controlled;

b) Providing at least one premanufactured testing device (1), representative of one of the sub-components of the structure;

c) Bonding said at least one premanufactured testing device (1) to the other sub-component (7) of the structure in conditions similar to those of the real adhesive joint of said sub-components;

d) Carrying out at least one mechanical test on said at least one premanufactured testing device (1) which allows assessing the quality of said adhesive joint. Both the qualitative (failure mode) and the quantitative (failure stress and strain) results are considered as representative of the real adhesive joint in this test.

In a preferred embodiment of the invention, the procedure object of the present invention is applied to structures made of composite materials.

In another preferred embodiment, the procedure object of the present invention is applied to structures made of metallic materials.

An advantage of the present invention with respect to the quality control processes using standard test coupons is that it allows replacing the manufacture and testing of said standard test coupons with the incorporation of small premanufactured devices representative of one of the sub-components of the joint which are bonded to the other sub-component in conditions similar to those of the real joint. The quality of the joint between sub-components is represented by the quality of the joint between the premanufactured device and the other sub-component, which is given by the stress necessary to cause the failure of the joint between both in a test which can be carried out in situ immediately after the manufacturing process, greatly simplifying and reducing the cost of the qualification process of said joints.

Other features and advantages of the present invention will be disclosed in the following detailed description of an illustrative embodiment of the object with respect to the attached drawings.

DETAILED DESCRIPTION OF THE INVENTION

Figure 1:
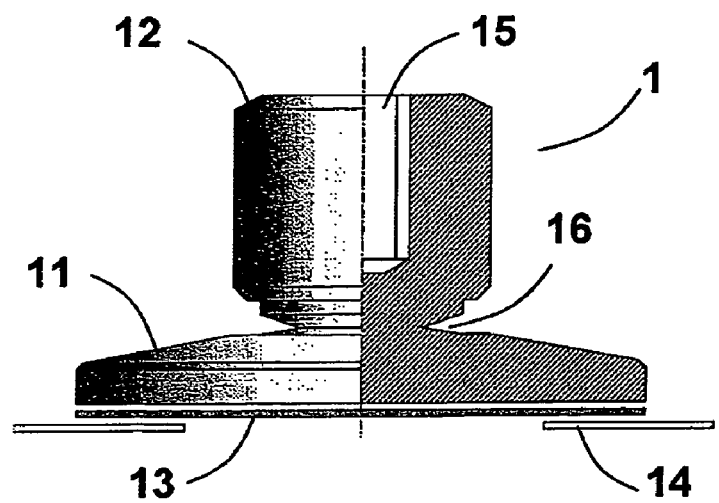
FIG. 1 shows an elevational view with a partial section of a device 1 used in a quality control process according to the present invention, formed by a main body 11 which will be fixed to the surface of the element to be tested, and a disposable head 12 incorporating an indentation or housing for a tool—in the figure, a cylindrical housing 15 of hexagonal section for an Allen wrench—joined through a frangible neck 16. The main body 11 has a planar surface which will be the joining surface with the surface of the element to be tested, on which the joining adhesive 13, which may or may not be incorporated in the device itself, and a non-adherent release film 14—of polytetrafluoroethylene or the like—which may or may not be incorporated in the device itself, will be applied and will be partially interposed between the device 1 object of the invention and the surface of the element to be tested.
Figure 2:
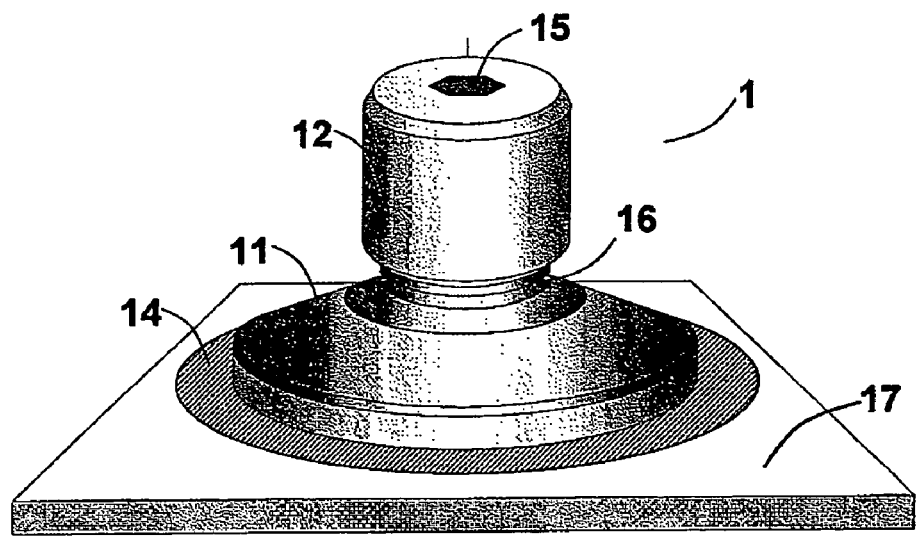
FIG. 2 shows an isometric projection view of the device 1 installed on the surface of the element 17 to be tested.
Figure 3:
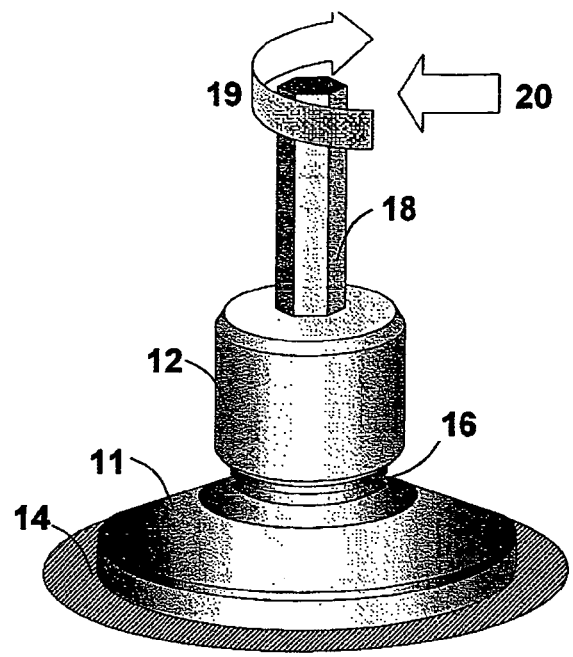
FIG. 3 shows the same view as FIG. 2 and depicts the rod of the tool 18 introduced in its housing 15 and by means of which two cases of different loads can be applied on the device, each stress represented by means of an arrow: a torque 19 on the axis of symmetry of the device and a stress 20 with its corresponding resulting bending moment in the notch of the frangible neck 16.

FIGS. 1 and 2 show a front view with a partial section and an isometric projection view of the premanufactured testing device 1 used in a preferred embodiment of the present invention object of the invention, the function of which is to replace the standard test coupons used to certify the quality of structural adhesive joints. The device 1 allows testing the quality of co-bonded joints (adhesive joints between precured elements of composite material and elements of composite material without curing) and secondary bonded joints (adhesive joints between precured elements of composite material or solid metallic and/or non-metallic elements generally).

The device 1 is formed by a main body 11 which will be fixed to the surface of the element 17 to be tested and a disposable head 12 joined through a frangible neck 16. The head 12 incorporates an indentation or housing 15 for introducing a tool 18 in it, for example an Allen wrench.

The main body 11 of the device has a planar surface which will be the joining surface with the surface of the element 17 to be tested, on which the joining adhesive 13, which may or may not be incorporated in the device itself, and a non-adherent release film 14—of polytetrafluoroethylene or the like—which may or may not be incorporated in the device 1 itself, will be applied and will be partially interposed between the device 1 object of the invention and the surface of the element 17 to be tested.

The non-adherent release film 14 has a multiple function: it controls the area of the bonded surface, it prevents the formation of an adhesive meniscus causing the strength of the joint to vary, and it causes a notch effect on the joint.

The device 1 can be made of a metallic material, a composite material, a plastic material or of several of them.

For a single configuration of the device 1, the type of adhesive used and its application conditions influence the representative nature thereof:

a) If the adhesive is incorporated in the device 1 before it is supplied and if it is different from the adhesive of the represented adhesive joint, or it is the same but of a different batch, or it has been subjected to different storage conditions and/or it is applied in the same conditions, the results of the test will be representative of the quality of the surface preparation of the element on which it has been bonded.

b) If the adhesive is incorporated after it is supplied, is identical to the adhesive of the represented adhesive joint, is extracted from the same batch, has been subjected to the same storage conditions and is applied in the same conditions, the results of the test will be representative of the quality of the surface preparation and of the condition of the adhesive used.

In any case, it is recommendable to use the same type of adhesive in the device 1 as the one used in the represented joint or at least an adhesive with similar processability conditions and mechanical properties and always with a shearing strength and toughness greater than that of the frangible neck 16 of the device 1.

Figure 4:
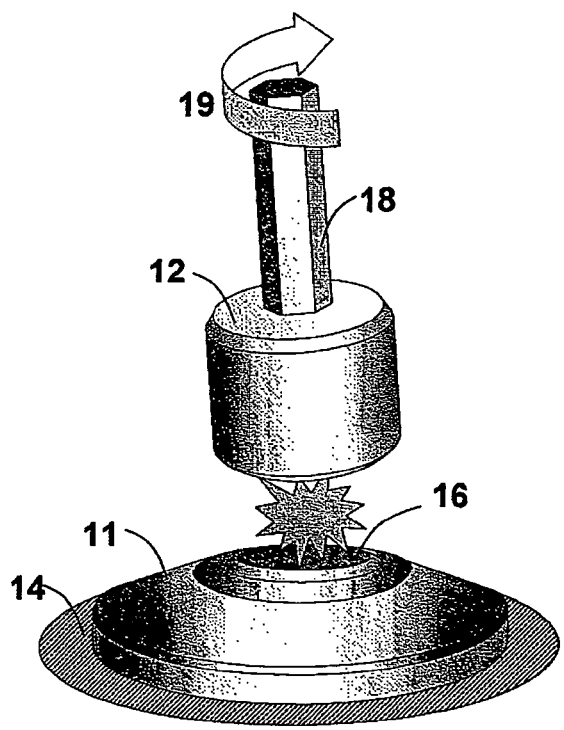
FIG. 4 shows the same view as FIG. 3 and schematically shows the application of a torque 19 on the axis of symmetry of the device 1 causing the fracture of the frangible neck 16 and the detachment of the disposable head 12, characteristic of a correct adhesive joint.

The configuration of the device 1 allows considering three possible tests:

i) Shearing strength test of the adhesive by applying a torque 19 on the axis of symmetry of the device 1. The torsional strength of the frangible neck 16 will be set such that it breaks with a torque slightly lower than the one estimated for the failure of the adhesive joint. If the torque 19 is applied with a simple non-dynamometric tool, the test will be qualitative and will have several possible results:

If device 1 breaks at the frangible neck 16 (see FIG. 4), the quality of the joint is good and the main body remains adhered to the structural element as evidence.

Figure 5:
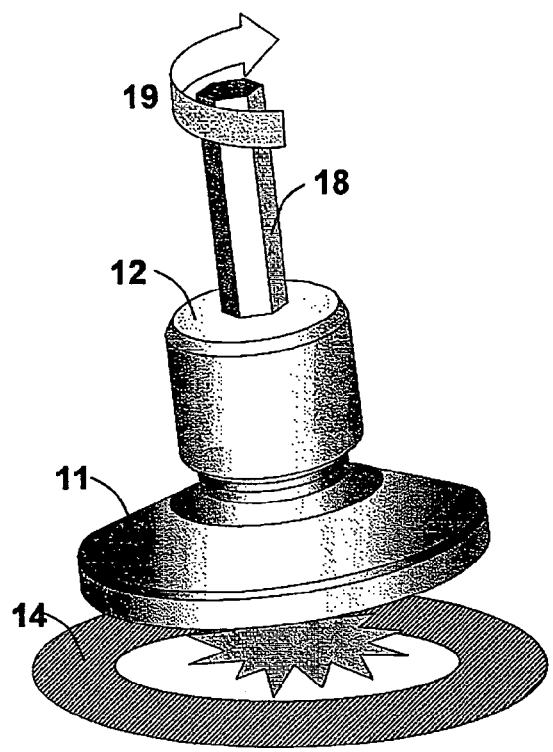
FIG. 5 shows the same view as FIG. 3 and schematically shows the application of a torque 19 on the axis of symmetry of the device 1 causing the debonding of the main body 11 of the device 1, characteristic of an defective joint.
Figure 6:
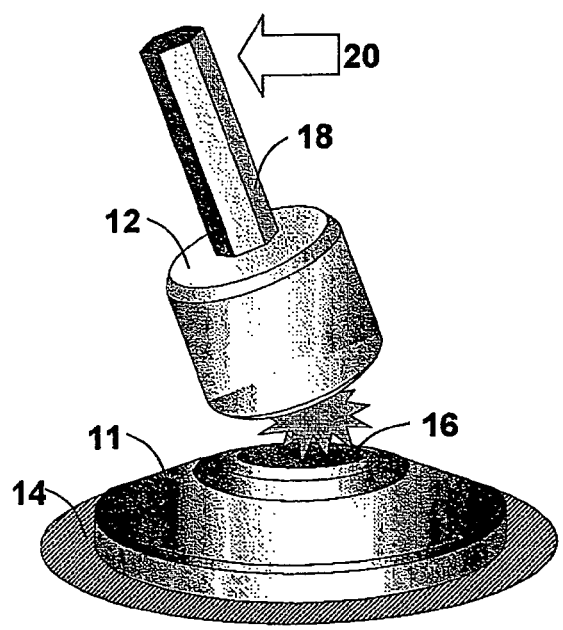
FIG. 6 shows the same view as FIG. 4 and schematically shows the application of a stress 20 perpendicular to the axis of symmetry of the device 1 which will cause a resulting bending moment in the notch of the frangible neck 16, giving rise to the fracture of the latter and the detachment of the disposable head 12 indicating a correct adhesive joint.
Figure 7:
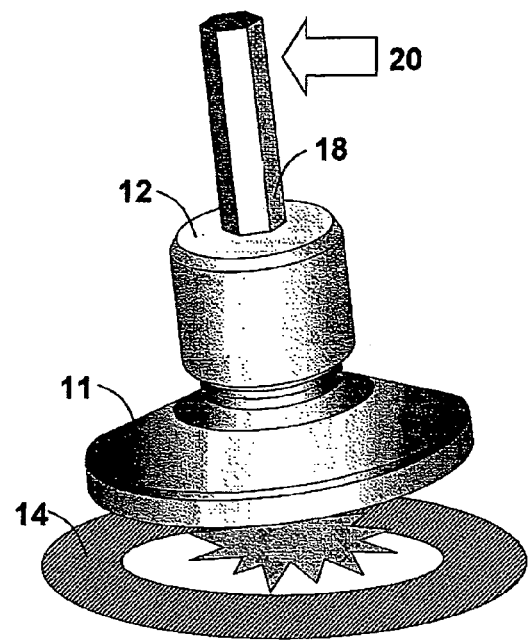
FIG. 7 shows the same view as FIG. 5 and schematically shows the application of a stress 20 perpendicular to the axis of symmetry of the device 1 which will cause a resulting bending moment in the notch of the frangible neck 16, giving rise to the debonding of the main body 11 of the device, characteristic of a defective adhesive joint.
Figure 8:
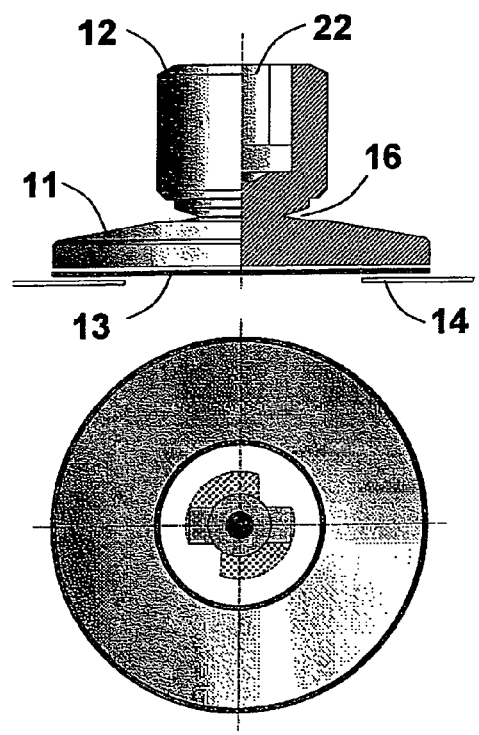
FIG. 8 shows a plan elevational view of a partial section of the device 1 object of the invention with a housing 22 in the form of a hook or key alternative to the Allen type hexagonal housing 15. This new configuration allows the application of tension in the direction of the axis of symmetry of the device 1.

If the device 1 is completely detached from the structural element (see FIG. 5) without the fracture of the frangible neck 16, there are 3 cases to be considered:

1. Adhesive failure: the adhesive remains adhered to the surface of the device indicating a bad quality of the surface preparation and therefore a defective joint.

2. Cohesive failure: the adhesive remains distributed between the surface of the structural element and the device, indicating a shearing strength of the adhesive lower than the required minimum. Assuming a correct choice of the device, it can only occur in configuration b), indicating a bad choice of the adhesive, or the deterioration thereof, and therefore a defective joint.

3. Failure due to fracture or delamination of the structural element, indicating an oversizing of the adhesive joint or the deterioration of the substrate before or during the surface preparation.

Figure 9:
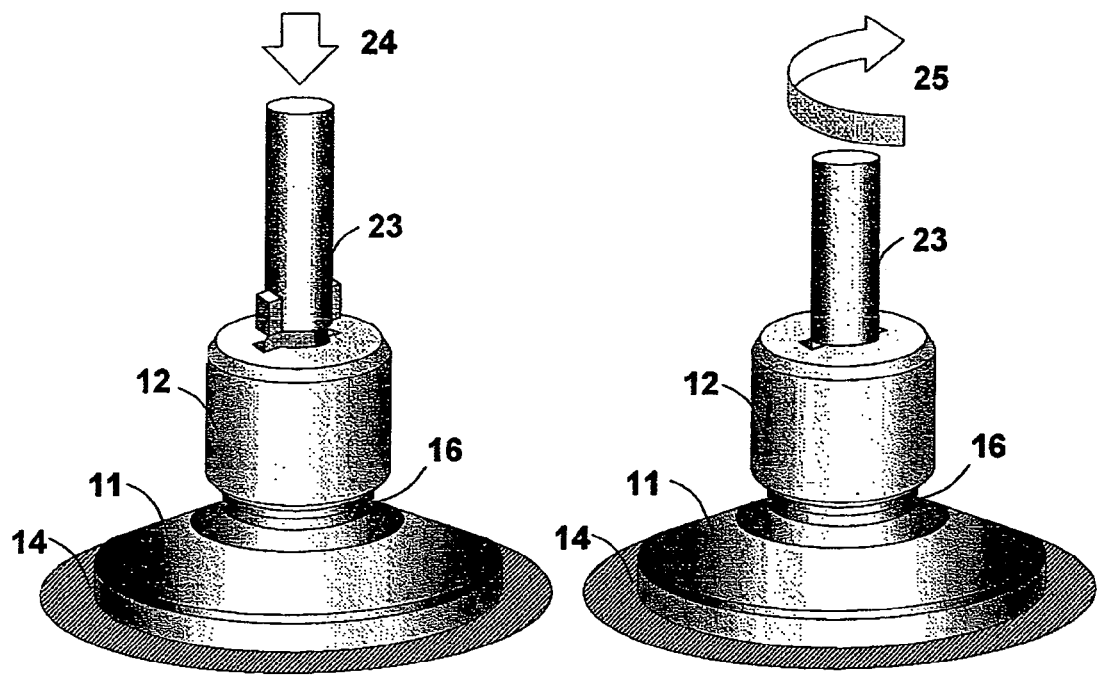
FIG. 9 shows an isometric projection view of the device 1 with a tool 23 introduced in the housing 22 in the form of a hook or key. The tool 23 is introduced in the housing 22 of the head 12 with a translational movement 24 and it is blocked with a quarter-turn rotation 25 on the axis thereof.
Figure 10:
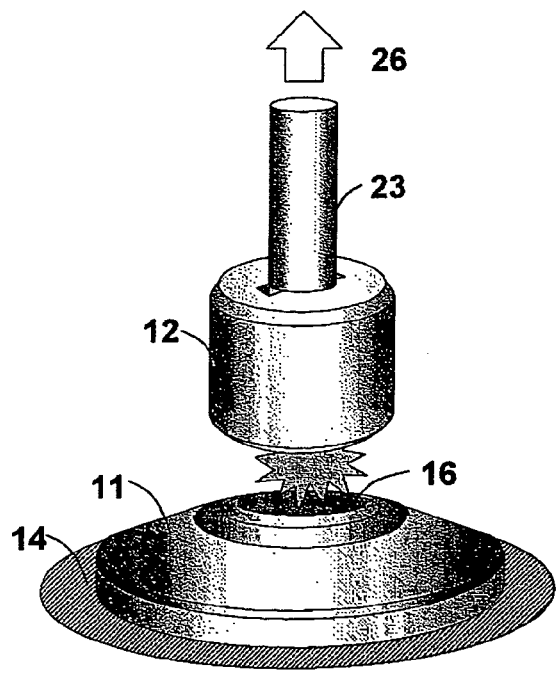
FIG. 10 shows the same view as FIG. 9 and schematically shows the application of a tensile stress 26 causing the fracture of the frangible neck 16 and the detachment of the head 12 indicating a correct adhesive joint.
Figure 11:
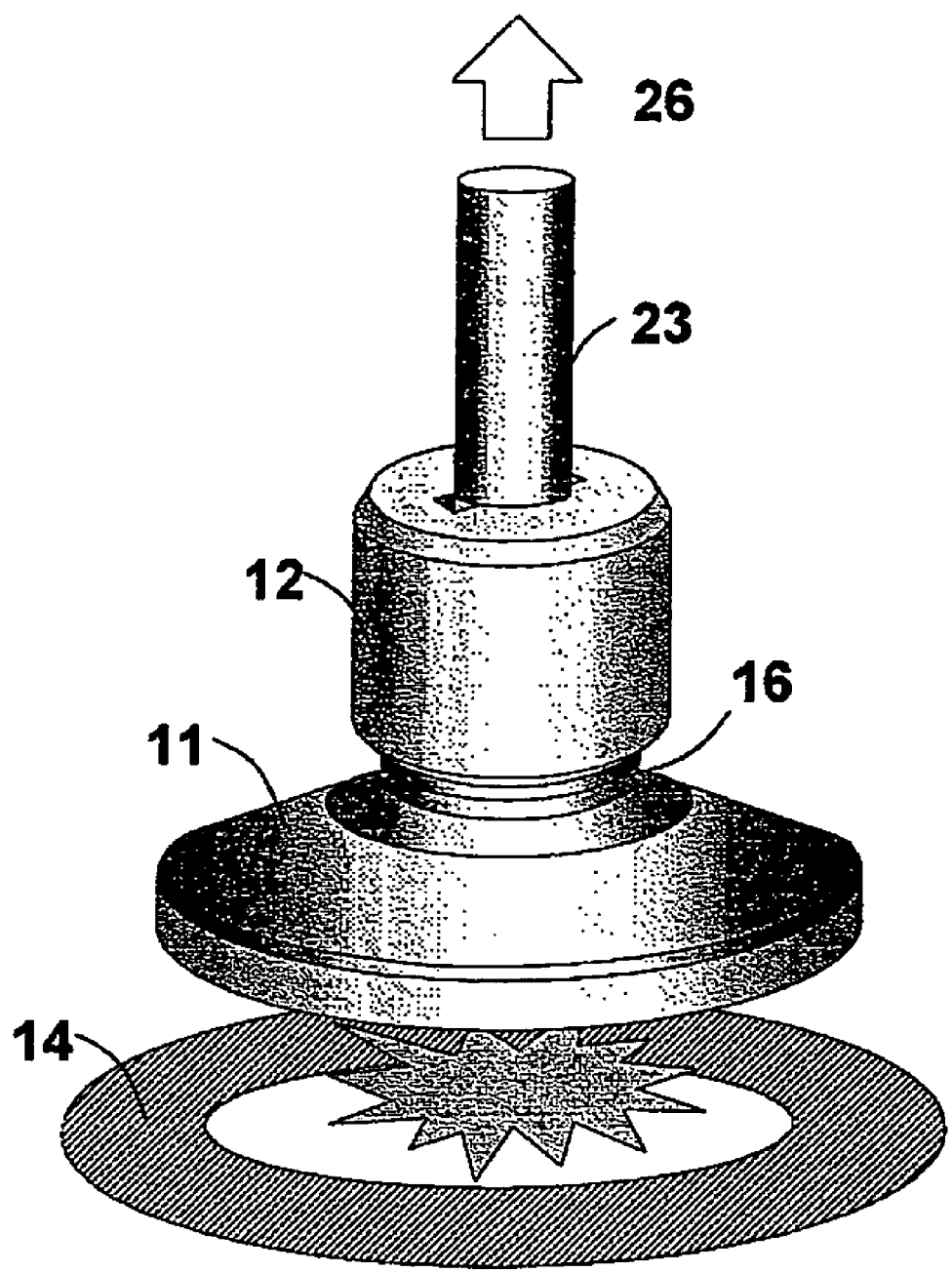
FIG. 11 shows the same view as FIG. 9 and schematically shows the application of a tensile stress 26 causing the debonding of the main body 11 of the device 1, characteristic of a defective adhesive joint.

If a dynamometric tool is used, the test will have a quantitative result which will provide additional information on the real strength of the joint.

ii) Fracture toughness test of the adhesive: applying a stress 20 on the axis of symmetry of the device 1. The bending strength of the device 1 in the frangible neck 16 will be set such that it breaks with a stress slightly less than the one estimated for the failure of the adhesive joint. If the stress 20 is applied with a non-dynamometric tool, the test will be qualitative and will have the same possible results as the shearing strength test. If a dynamometric tool is used, the test will have a quantitative result, which will provide additional information on the real strength of the joint.

iii) Tensile test (see FIG. 9, 10 and 11). It requires a hook or key type housing 22 suitable for the use of a tool 23 which allows applying tension 16 on the device 1. The tool 23 is introduced in the housing 22 of the head 12 with a translational movement 14 and it is blocked with a quarter-turn rotation 15 on the axis thereof. The tensile strength of the device 1 in the frangible neck 16 will be set such that it breaks with a stress slightly less than the one estimated for the failure of the adhesive joint. If the tension 26 is applied with a non-dynamometric tool, the test will be qualitative and will have the same possible results as the shearing strength test. If a dynamometric tool is used, the test will have a quantitative result which will provide additional information on the real strength of the joint.

The process object of the present invention can be carried out with devices premanufactured in a different manner from the one depicted in FIG. 1 and particularly without the frangible neck 16, although in this case, the use of dynamometric tools would be necessarily required for the tests.

Those modifications comprised within the scope defined by the following claims can be introduced in the preferred embodiment which has just been described.

The invention claimed is:

1. A quality control process for evaluating an adhesive join between a first sub-component and a second sub-component of a composite material structure, the process comprising the steps of:
    providing at least one premanufactured tested device representative of the first sub-component of the structure, the at least one premanufactured testing device comprising a body having a planar lower surface, a head, and a frangible neck between the head and the body;
    providing an adhesive between the planar lower surface of said at least one premanufactured testing device and a surface of the second sub-component of the structure;
    providing a non-adherent release film partially interposed between the surface of said at least one premanufactured testing device and said surface of the second sub-component of the structure;
    bonding the at least one premanufactured testing device to the second sub-component to form a test joint under conditions that provides the test joint with a quality that is representative of a quality of the adhesive joint of the sub-components; and
    after bonding, carrying out at least one mechanical test on said at least one premanufactured testing device until either the testing device separates at the frangible neck or the testing device separates from the second sub-component.

2. A quality control process according to claim 1, wherein said at least one mechanical test is one of the following: a shearing strength test, a fracture toughness test and a tensile test.

3. A quality control process according to claim 2, wherein the mechanical test is carried out by applying a non-dynamometric tool to the premanufactured testing device.

4. A quality control process according to claim 2, wherein the mechanical test is carried out by applying a dynamometric tool to the premanufactured testing device.

5. A quality control process according to claim 1, wherein
    the head includes a housing for receiving a tool which transmits a mechanical stress to the premanufactured testing device;
    and the frangible neck is sized to break when said mechanical stress reaches a predetermined magnitude.

6. A quality control process according to claim 5, wherein the body, the head and the neck of the premanufactured testing device (1) are configured as bodies of revolution about an axis of symmetry.

7. A quality control process according to claim 6, wherein said mechanical stress is a torque applied to the testing device through said tool.

8. A quality control process according to claim 6, wherein the mechanical stress is a side stress applied to the testing device through said tool.

9. A quality control process according to claim 6, wherein the mechanical stress is an axial stress applied to the testing device through said tool.

10. A quality control process according to claim 1, wherein the sub-components are made of a metallic material.

11. A quality control process according to claim 1, wherein the sub-components are made of a composite material.

12. A quality control process according to claim 11, wherein the composite material structure is an aeronautical structure formed by a skin reinforced by stringers, the testing device being representative of the stringers.

13. A structure which has been evaluated by the quality control process according to claim 1.

14. A quality control process according to claim 1, wherein the adhesive is provided on the planar lower surface of the testing device and the non-adherent release film is provided between the adhesive and the surface of the second sub-component.

* * * * *

UNITED STATES PATENT AND TRADEMARK OFFICE
CERTIFICATE OF CORRECTION

| | | |
|---|---|---|
| PATENT NO. | : 7,497,115 B2 | Page 1 of 1 |
| APPLICATION NO. | : 11/516028 | |
| DATED | : March 3, 2009 | |
| INVENTOR(S) | : Jose Manuel Menendez Martin et al. | |

It is certified that error appears in the above-identified patent and that said Letters Patent is hereby corrected as shown below:

On the Title Page, Item (30) the foreign application priority data should read:

June 30, 2006 PCT/ES06/70092

Signed and Sealed this
Twelfth Day of April, 2011

David J. Kappos
*Director of the United States Patent and Trademark Office*